US011207433B2

(12) United States Patent
Liu et al.

(10) Patent No.: US 11,207,433 B2
(45) Date of Patent: Dec. 28, 2021

(54) IMAGING AGENTS AND USES THEREOF

(71) Applicants: Yongjian Liu, St. Louis, MO (US); Pamela K. Woodard, St. Louis, MO (US)

(72) Inventors: Yongjian Liu, St. Louis, MO (US); Pamela K. Woodard, St. Louis, MO (US)

(73) Assignee: Washington University, St. Louis, MO (US)

(*) Notice: Subject to any disclaimer, the term of this patent is extended or adjusted under 35 U.S.C. 154(b) by 0 days.

(21) Appl. No.: 16/449,147

(22) Filed: Jun. 21, 2019

(65) Prior Publication Data

US 2019/0388570 A1 Dec. 26, 2019

Related U.S. Application Data

(60) Provisional application No. 62/687,934, filed on Jun. 21, 2018.

(51) Int. Cl.
  *A61K 51/08* (2006.01)
  *A61K 51/02* (2006.01)
  *A61K 51/12* (2006.01)
  *G01T 1/29* (2006.01)

(52) U.S. Cl.
  CPC .......... *A61K 51/088* (2013.01); *A61K 51/025* (2013.01); *A61K 51/1244* (2013.01); *G01T 1/2985* (2013.01)

(58) Field of Classification Search
  CPC ...... A61K 51/00; A61K 51/08; A61K 51/088; A61K 51/025; A61K 51/1244; G01T 1/2985
  USPC .......... 424/1.11, 1.49, 1.65, 1.69, 1.81, 1.85, 424/1.89, 9.1, 9.2, 9.3, 9.4, 9.42, 9.43; 514/1, 1.1, 19.2, 19.3, 19.4, 19.5, 19.6, 514/19.7, 19.8, 19.9, 20.9, 21.1
  See application file for complete search history.

(56) References Cited

U.S. PATENT DOCUMENTS

| | | | | |
|---|---|---|---|---|
| 8,436,140 | B2 * | 5/2013 | Woodard | A61K 49/085 530/327 |
| 2003/0199000 | A1 | 10/2003 | Valkirs et al. | |
| 2011/0300071 | A1 | 12/2011 | Woodard et al. | |
| 2017/0095577 | A1 | 4/2017 | Woodard et al. | |

OTHER PUBLICATIONS

Pressly et al, Bioconjugate Chemistry, vol. 24, pp. 196-204 (Year: 2013).*
An et al, J. Am. Chem. Soc., vol. 137, pp. 8412-8418 (Year: 2015).*
Qu et al, J. Phys. Chem. C, vol. 117, pp. 3548-3555 (Year: 2013).*
Dijkgraaf I., et al., "Radionuclide Imaging of Tumor Angiogenesis," 2009, Cancer Biotherapy Radiopharmaceuticals, 24:637-647, 13 pages.
Dillon, C.P., et al., "RNAI as an Experimental and Therapeutic Tool to Study and Regulate Physiological and Disease Processes," 2005, Ann Rev of Physiol, 67:147-173, Abstract Only, 1 page.
Dykxhoorn, D.M., et al., "The Silent Revolution: RNA Interference as Basic Biology, Research Tool, and Therapeutic," 2005, Ann Rev Med, 56:401-423, 25 pages.
Elhai, J., et al., "Conjugal Transfer of DNA to Cyanobacteria," 1988, Meth Enzym, 167:747-754, Abstract Only, 1 page.
Fanning, G.C., et al., "Gene-Expressed RNA as a Therapeutic: Issues to Consider, Using Ribozymes and Small Hairpin RNA as Specific Examples," RNA Towards Medicine, Handb Exp Pharmacol. 173:289-303, Abstract Only, 1 page.
Ghadessy, F.J., et al., "Directed Evolution of Polymerase Function by Compartmentalized Self-Replication," 2001, Proc Natl Acad Sci USA, 98/8:4552-4557, 6 pages.
Helene, C., et al., Control of Gene Expression by Triple Helix-Forming Oligonucleotides, The Antigene Strategy,: 1992, Ann NY Acad Sci, 660:27-36, Abstract Only, 2 pages.
Kong, X., et al., "Natriuretic Peptide Receptor A as a Novel Anticancer Target," 2008, Cancer Res, 68/1:249-256, 9 pages.
Lee, H-J., et al., "Biomarker Discovery From the Plasma Proteome Using Multidimensional Fractionation Proteomics," 2006, Curr Opin Chem Biol, 10/1:42-49, Abstract Only, 1 page.
Link, A. J., et al. Beyond Toothpicks: New Methods for Isolating Mutant Bacteria,: 2007, Nature Reviews 5/:680-688, Abstract Only, 1 page.
Liu, Y., et al. "PET Imaging of Chemokine Receptors in Vascular Injury-Accelerated Atherosclerosis," 2013, J Nucl Med, 54:1135-1141, 8 pages.
Liu, Y., et al. "Molecular Imaging of Atherosclerotic Plaque with (64)Cu-Labeled Natriuretic Peptide and PET," 2010, J Nucl Med, 51:85-91, 8 pages.
Maack, T., et al., "Physiological Role of Silent Receptors of Atrial Natriuretic Factor," 1987, Science 238: 675-678, Abstract Only, 1 page.
Maack, T., "The Broad Homeostatic Role of Natriuretic Peptides," 2006, Arq Bras Endocrinol Metabol, 50:198-207, 10 pages.
Maher, L.J., III, "DNA Triple-Helix Formation: An Approach to Artificial Gene Repressors," 1992, Bioassays 14/12:807-815, Abstract Only, 1 page.
Pushparaj, P.N., et al. "Short Intefering RNA (siRNA) as a Novel Therapeutic," 2006, Clinical and Experimental Pharmacology and Physiology, 33/5-6:504-510, 7 pages.
Reynolds, A., et al., "Rational siRNA Design for RNA Interference," 2004, Nature Biotechnology, 22/3:326-330, Abstract Only, 1 page.
Sagner, G., et al., "Rapid Filter Assay for the Detection of DNA Polymerase Activity: Direct Identification of the Gene for the DNA Polymerase from Thermus aquaticus," 1991 Gene, 97/1:119-123, Abstract Only, 1 page.

(Continued)

*Primary Examiner* — D. L. Jones
(74) *Attorney, Agent, or Firm* — Stinson LLP

(57) ABSTRACT

The present invention relates to various compositions and methods of using these compositions for imaging natriuretic peptide receptors using, for example, positron emission tomography.

19 Claims, 8 Drawing Sheets
(8 of 8 Drawing Sheet(s) Filed in Color)
Specification includes a Sequence Listing.

(56) References Cited

OTHER PUBLICATIONS

Sethi, A., et al. "PET Imaging of NPRC Receptor Using Targeted Nanoclusters in a Mouse Angiogenesis Model," 2018, J Nucl Med, 59/Supp 1:1070, Abstract Only, 1 page.
Studier, F.W., "Protein Production by Auto-Induction in High-Density Shaking Cultures," 2005, Protein Expr Purif, 41/1:207-234, Abstract Only, 1 page.
Vesely, D. L., "Atrial Natriuretic Peptides: Anticancer Agents," 2005, J Investig Med, 53/7: 360-365, Abstract Only, 1 page.
Woodard, G.E., et al. "Chapter 3 Natriuretic Peptides in Vasular Physiology and Pathology," 2008, Int'l Review Cell Mol Biol 268:59-93, Abstract Only, 1 page.
Zhao, Y., et al., "Gold Nanoclusters Doped with 64Cu for CXCR4 Positron Emission Tomography Imaging of Breast Cancer and Metastasis," 2016, ACS Nano, 10/6:5959-5970, 26 pages.
Zhao, Y., et al., "Facile synthesis, pharmacokinetic and systemic clearance evaluation, and positron emission tomography cancer imaging of 64Cu-Au alloy nanoclusters," 2014, Nanoscale, 6/22:12501-9, (Accepted Manuscript) 26 pages.

\* cited by examiner

⁶⁴Cu AuNCs-CANF: DLS

⁶⁴CuAuNCs-CANF: Zeta Potential 20 nm

IMAGING AGENTS AND USES THEREOF

CROSS REFERENCE TO RELATED APPLICATIONS

This application claims priority to U.S. Provisional Application Ser. No. 62/687,934, filed Jun. 21, 2018, which is incorporated herein by reference in its entirety.

STATEMENT REGARDING FEDERALLY SPONSORED RESEARCH OR DEVELOPMENT

This invention was made with Government support under HHSN268201000046C awarded by the National Institutes of Health. The Government has certain rights in the invention.

INCORPORATION BY REFERENCE OF SEQUENCE LISTING

The Sequence Listing, which is a part of the present disclosure, includes a computer readable form and a written sequence listing comprising nucleotide and/or amino acid sequences. The sequence listing information recorded in computer readable form is identical to the written sequence listing. The subject matter of the Sequence Listing is incorporated herein by reference in its entirety.

FIELD OF THE INVENTION

The present invention relates to various compositions and methods of using these compositions for imaging natriuretic peptide receptors using, for example, positron emission tomography.

BACKGROUND

Antiangiogenic therapy in conjunction with traditional chemotherapy and radiation represents a major step towards more selective and better-tolerated cancer treatments. However, there remains a need for imaging probes that permit sensitive detection and characterization of tumor angiogenesis and provide a means of following the progress of antiangiogenic tumor treatments. Similarly, there is also a need for imaging probes that permit sensitive detection and characterization of atherosclerosis including atherosclerotic plaque, and provide a means of following the progress of treatments. Currently, most diagnostic modalities used for imaging atherosclerotic plaques assess the severity of the stenosis and/or plaque morphology. These tests include x-ray angiography, computed tomographic (CT) angiography, magnetic resonance imaging and intravascular ultrasound. Several radionuclide-based approaches for non-invasive, functional imaging of atherosclerosis have been developed and evaluated in animal models. Among the tracers for plaque imaging, those containing γ-emitters (technetium-99m, indium-111, iodine-123, etc.) suffer from the limited spatial resolution of single photon emission tomography (SPECT). In contrast, because of superior spatial resolution, positron emission tomography (PET) is more suitable for plaque imaging.

Natriuretic peptides (NPs) are a family of cardiac- and vascular-derived hormones that play a relevant role in cardiovascular homeostasis (Woodard G E, et al. Int rev Cell Mol. Biol. 268:59-93, 2008). Among the four family members, atrial natriuretic peptide (ANP) and C-type natriuretic peptide (CNP) have been demonstrated to suppress the signaling of vascular endothelial growth factor (VEGF), a key regulator of angiogenesis (Dijkgraaf I, et al. Cancer Biother. Radiopharm. 24: 637-647, 2009). Furthermore, ANP has been reported to attenuate the angiogenesis process (Kong, X., et al., Cancer Res. 68: 249-256, 2008; Vesely, D. L., J. Investig. Med. 53: 360-365, 2005). The natriuretic peptides exert their biological effects through their interaction with natriuretic peptide receptors (NPRs) (Maack, T., et al., Science 238: 675-678, 1987). Among the NPRs, the clearance receptor (NPR-C) constitutes approximately 95% of the entire NPR population. In addition, NPR-C is the only NPR that recognizes all the NPs as well as NP fragments containing as few as five conserved amino acids (Arg-Ile-Asp-Arg-Ile) (Maack, T., Arq. Bras. Endocrinol. Metabol. 50: 198-207, 2006).

Patients with carotid atherosclerosis are often asymptomatic and at an unknown risk for stroke. It has been shown that the NPR-C receptor is up-regulated in complex and histologically unstable human carotid artery plaques. Imaging agents containing the natural ligand for the NPR-C receptor (i.e., C-atrial natriuretic peptide (CANF)) have been used for specific positron emission tomography (PET) imaging of this receptor. For example, a CANF peptide functionalized polymeric nanoparticle ($^{64}$Cu-DOTA-CANF-Comb) can be used as described in U.S. Patent Application Publication No. 2011/0300071. However, the extended blood retention of this radiotracer secondary to the comb composition results in a relatively long (~12 hr) delay from injection to optimal PET imaging time.

Therefore, there remains a need for imaging agents that exhibit improved blood clearance time to reduce imaging delays. Such imaging agents can be useful for assessing angiogenesis and atherosclerosis in patients suffering from cancer, cardiovascular disease or other conditions.

BRIEF SUMMARY

Various aspects of the present invention relate to compositions comprising a nanocluster comprising a positron-emitting radionuclide and gold, a natriuretic peptide or fragment thereof, and a linking group complexed with the nanocluster and bonded to the natriuretic peptide or fragment thereof.

Further aspects relate to various methods of using these compositions as imaging agents in imaging platforms. For example, some aspects of the present invention relate to methods of determining a distribution of a C-atrial natriuretic peptide receptor or for imaging an atherosclerotic plaque or angiogenesis in a subject. The methods comprise administering to the subject a composition or imaging agent comprising a composition as described herein and then subjecting the subject to an imaging procedure.

Other objects and features will be in part apparent and in part pointed out hereinafter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Corresponding reference characters indicate corresponding parts throughout the drawings.

DETAILED DESCRIPTION

Figure 1A:
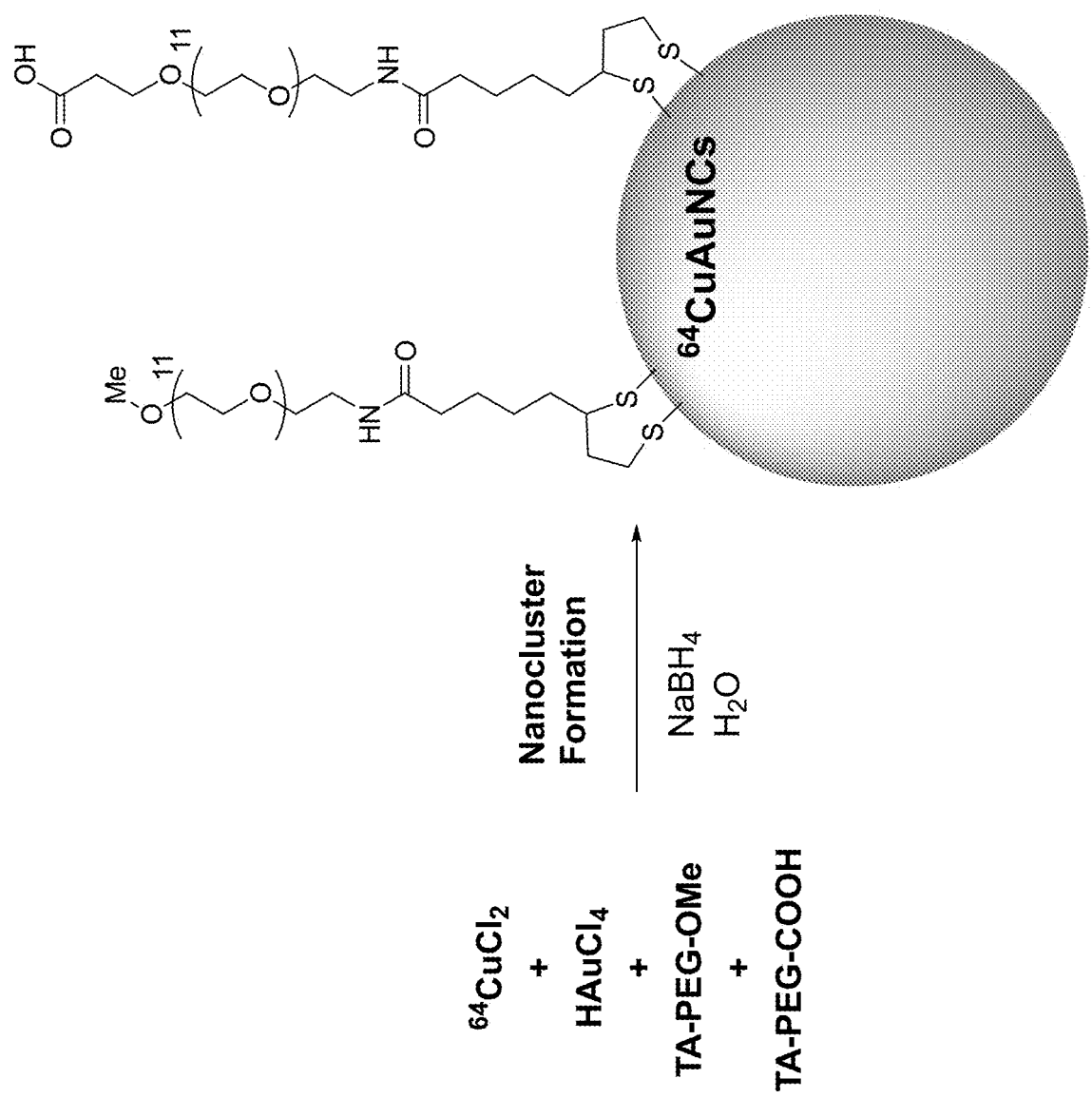
FIG. 1A shows a schematic illustrating the formation of $^{64}$Cu—Au nanoclusters and conjugation with TA-PEG-COOH and TA-PEG-OMe.

The present invention generally relates to various compositions and methods of using these compositions for imaging natriuretic peptide receptors using, for example, positron emission tomography. For example, the compositions described herein may be formulated as imaging agents (e.g., for use with PET imaging). The compositions and imaging agents comprising the compositions can target NPR-C receptors compositions and can exhibit reduced blood retention thereby providing for faster/earlier imaging after administration (e.g., at 4 hours vs. 12 hours after injection). Faster/earlier imaging after administration is advantageously more convenient for patients and medical personnel.

Various compositions of the present invention comprise a nanocluster comprising a positron-emitting radionuclide and gold; a natriuretic peptide or fragment thereof; and a linking group complexed with the nanocluster and bonded to the natriuretic peptide or fragment thereof.

In various embodiments, the positron-emitting radionuclide is a metal isotope. In some embodiments, the positron emitting radionuclide is selected from the group consisting of iron-52, copper-62, copper-64, zinc-62, zinc-63, gallium-68, rubidium-82, yttrium-86, zirconium-89, technetium-94m, and indium-110m. For example, the positron-emitting radionuclide can be selected from the group consisting of iron-52, copper-62, copper-64, zinc-62, zinc-63, gallium-68, and zirconium-89. In various embodiments, the positron-emitting radionuclide comprises copper-64. In certain embodiments, the composition comprises an alloy of the positron-emitting radionuclide and gold.

In various embodiments, the natriuretic peptide or fragment thereof (e.g., an oligopeptide) has an amino acid sequence comprising Arg-Ile-Asp-Arg-Ile (SEQ ID NO: 1).

In various embodiments, the natriuretic peptide or fragment thereof further comprises at least two cysteine residues and can comprise in various configurations, at least one cysteine (i.e., a sulfur containing amino acid residue obtained by the formation of a disulfide bond between two cysteine residues). In some other configurations, the cysteines can be in reduced form (i.e., not including a disulfide bridge). Accordingly, in some embodiments, the natriuretic peptide or fragment thereof has an amino acid sequence comprising Cys-Phe-Gly-Gly-Arg-Ile-Asp-Arg-Ile-Gly-Ala-Cys-NH$_2$ (SEQ ID NO: 2), in which the carboxy terminus is amidated and where the cysteines form a disulfide linkage. In further embodiments, the natriuretic peptide or fragment thereof has an amino acid sequence comprising Arg-Ser-Ser-[Cys-Phe-Gly-Gly-Arg-Ile-Asp-Arg-Ile-Gly-Ala-Cys]-NH$_2$ (SEQ ID NO: 3), where the carboxy terminus is amidated and the cysteines comprise a disulfide linkage. In various embodiments, the natriuretic peptide or fragment thereof comprises C-atrial natriuretic peptide (CANF).

In various embodiments, the natriuretic peptide or fragment comprises no more than 25, no more than 23, no more than 20, no more than 15, no more than 10, or no more than 6 amino acids. For example, the natriuretic peptide or fragment thereof can comprise no more than 23 amino acids.

As noted, the composition also comprises a linking group. In various embodiments, the linking group comprises a functionalized polymer. In certain embodiments, the functionalized polymer comprises ethylene oxide (EO) repeating groups (i.e., polyethylene glycol). For example, in some embodiments, the functionalized polymer comprises from about 5 to about 20 EO groups or from about 10 to about 15 EO groups (e.g., 11 EO groups).

In some embodiments, the functionalized polymer further comprises one or more sulfur-containing moieties. In certain embodiments, the functionalized polymer comprises a thioctic acid moiety. In various embodiments, the sulfur-containing moiety of the linking group is complexed with the nanocluster. In some embodiments, the linking group is represented by the following moiety:

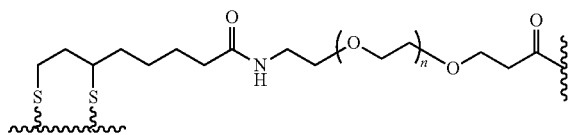

where n is an integer from about 5 to about 20 or from about 10 to about 15 (e.g., 11). The sulfur groups can be complexed with the nanocluster and the carboxyl terminus can be bonded to the N-terminus of the natriuretic peptide or fragment thereof (—NH—NP) as shown below:

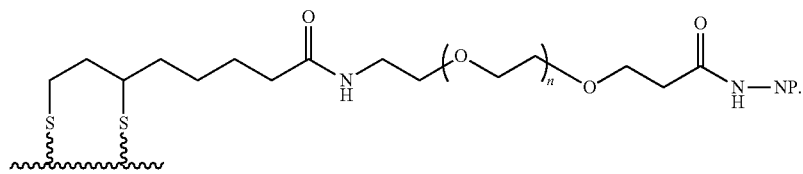

In some embodiments, the functionalized polymer has an average molecular weight of about 1 kDa to about 10 kDa, from about 3 kDa to about 8 kDa. For example, the functionalized polymer can have a molecular weight of about 5 kDa.

In some embodiments, the composition further comprises a surface modifier complexed with the nanocluster. In various embodiments, the surface modifier may be uncharged (neutral). In certain embodiments, the surface modifier can modulate the surface charge of the nanoclusters at close to neutral to provide for extended blood circulation and minimal non-specific interaction with serum proteins, cells or tissues in vivo.

In certain embodiments, the surface modifier also comprises a functionalized polymer. In various embodiments, the functionalized polymer of the surface modifier comprises ethylene oxide (EO) repeating groups (i.e., polyethylene glycol). For example, in some embodiments, the functionalized polymer of the surface modifier comprises from about 5 to about 20 EO groups or from about 10 to about 15 EO groups (e.g., 11 EO groups).

In various embodiments, the functionalized polymer of the surface modifier comprises an ether terminating group (e.g., —OMe). In some embodiments, the functionalized polymer of the surface modifier further comprises one or more sulfur-containing moieties. In certain embodiments, the functionalized polymer of the surface modifier comprises a thioctic acid moiety. In various embodiments, the sulfur-containing moiety of the surface modifier is complexed with the nanocluster. In some embodiments, the surface modifier is represented by the following moiety:

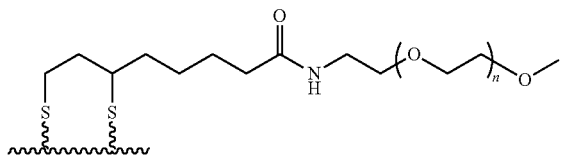

where n is an integer from about 5 to about 20 or from about 10 to about 15 (e.g., 11); and the sulfur groups are complexed with the nanocluster.

In some embodiments, the functionalized polymer of the surface modifier has an average molecular weight of about 1 kDa to about 10 kDa, from about 3 kDa to about 8 kDa. For example, the functionalized polymer can have a molecular weight of about 5 kDa.

The ratio of the linking group to the surface modifier can affect properties of the compositions such as size, surface charge, and in vivo behavior such as biodistribution and targeting efficiency. For example, when the surface modifier is neutral it can balance a charged linking group (e.g., a carboxylic acid) and provide for extended blood circulation and minimal non-specific interaction with serum proteins, cells or tissues in vivo. In various embodiments, the composition has a molar ratio of the linking group to the surface modifier from about 0.5:1 to about 3:1, from about 1:1 to about 3:1, from about 1:1 to about 2:1, or from about 2:1 to about 3:1. In certain embodiments, the molar ratio of the linking group to the surface modifier can be about 1:1.

In various embodiments, the nanocluster has a particle size (i.e., diameter) of from about 1 nm to about 100 nm, from about 1 nm to about 50 nm, from about 1 nm to about 25 nm, from about 1 nm to about 15 nm, from about 1 nm to about 10 nm, or from about 2 to about 7 nm.

In accordance with various embodiments of the invention, an imaging agent is provided. The imaging agent can comprise any of the compositions described herein. In various embodiments, the imaging agent is a PET tracer. Suitable formulations that may be prepared in accordance with these embodiments of the invention are described in more detail herein below.

In various embodiments, when administered to a subject, the composition can have improved pharmacokinetics relative to a composition formulated without gold. For example, in some embodiments, the composition can exhibit improved renal clearance compared to a composition prepared without gold.

In various embodiments, the composition can bind a Natriuretic Peptide Receptor C (NPRC). In certain embodiments, the natriuretic peptide or fragment binds the Natriuretic Peptide Receptor C (NPRC). As such, the compositions can be used as imaging agents to track the distribution of such receptors in vivo. The compositions can also be used to identify or evaluate various conditions such as atherosclerosis, stenosis, angiogenesis based on the distribution pattern of the C-type atrial natriuretic peptide receptor.

Accordingly, various embodiments of the invention include a method for determining a distribution of C-type atrial natriuretic peptide receptor in a subject. The method comprises administering an imaging agent described herein (that is, one that comprises a composition provided above) to the subject and then subjecting the subject to a medical imaging procedure. The distribution of the C-type atrial natriuretic peptide receptor can then be used to evaluate various medical conditions (e.g., atherosclerosis and/or angiogenesis).

A method is also provided for imaging an atherosclerotic plaque or angiogenesis. In various embodiments, the method comprises administering an imaging agent described herein to a subject and then subjecting the subject to a medical imaging procedure. In various embodiments, the methods can further comprise evaluating the degree or severity of carotid atherosclerosis or arterial stenosis in the subject based on the imaged atherosclerotic plaque. In various embodiments, the methods can further comprise evaluating progression of a tumor or cancerous lesion based on the imaged angiogenesis.

In various embodiments, the medical imaging procedure used in the methods described herein comprises positron emission tomography (PET). In various embodiments, the imaging can occur significantly earlier than it would normally occur during standard procedures outside this invention. For example, in various embodiments, the imaging procedure occurs within about 4 hours of administration of the imaging agent to the subject.

In various embodiments, the methods described herein can further comprise providing the subject with a stent placement or endarterectomy.

In various embodiments, the compositions and imaging agents described herein can be used in a medical imaging procedure to identify which patients have carotid atherosclerotic plaque that could rupture and cause stroke (e.g., determine which patients need to undergo surgical plaque removal (carotid endarterectomy) or could be treated medically). Additional indications can be to assess whether a plaque in coronary arteries might rupture and cause a myocardial infarction (heart attack) or ischemia. Further, since this receptor (NPR-C) is also upregulated in some tumor types, (especially those with angiogenesis) the compositions and imaging agents herein may be further used to image cancer or tumors.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Md., 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

In various embodiments, the present invention provides a radiopharmaceutical composition comprising compositions as described herein together with a biocompatible carrier suitable for mammalian administration. The "biocompatible carrier" is a fluid, especially a liquid, in which the nanoparticulate composition of the invention is suspended or dissolved, such that the radiopharmaceutical composition can be administered to the mammalian body without toxicity or undue discomfort. The biocompatible carrier is suitably an injectable carrier liquid such as sterile water for injection; an aqueous solution such as saline; an aqueous solution of one or more tonicity-adjusting substances (e.g. salts of plasma cations with biocompatible counter-ions), sugars (e.g. glucose or sucrose), sugar alcohols (e.g. sorbitol or mannitol), glycols (e.g. glycerol), or other non-ionic polyol materials (e.g. polyethylene glycols, propylene glycols and the like). The biocompatible carrier may also comprise biocompatible organic solvents such as ethanol. Such organic solvents are useful to solubilize more lipophilic compounds or formulations. Preferably the biocompatible carrier is sterile water for injection, isotonic saline, or an aqueous ethanol solution. The pH of the biocompatible carrier for intravenous injection is suitably in the range 4.0 to 10.5.

When administered as a radiopharmaceutical composition (or imaging agent), the compositions described herein may be dosed according to the radioactivity therein (in Ci). For example, a suitable dose may be from about 10 µCi to about 10 mCi.

The formulation should suit the mode of administration. The agents of use with the current disclosure can be formulated by known methods for administration to a subject using several routes which include, but are not limited to, parenteral, pulmonary, oral, topical, intradermal, intratumoral, intranasal, inhalation (e.g., in an aerosol), implanted, intramuscular, intraperitoneal, intravenous, subcutaneous, intranasal, epidural, ophthalmic, transdermal, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 µm), nanospheres (e.g., less than 1 µm), microspheres (e.g., 1-100 µm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow co-localized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Molecular Biology

The compositions described herein comprise a natriuretic peptide. The peptide and any fragment thereof may be synthesized using standard techniques in the art, summarized herein.

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

Expression vector, expression construct, plasmid, or recombinant DNA construct is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the start site of transcription, such as, in the case of a polymerase II type promoter, a TATA element. A promoter can optionally include distal enhancer or repressor elements, which can be located as much as several thousand base pairs from the start site of transcription.

A "transcribable nucleic acid molecule" as used herein refers to any nucleic acid molecule capable of being transcribed into a RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present disclosure, conventional compositions and methods for preparing and using constructs and host cells are well known to one skilled in the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754).

The "transcription start site" or "initiation site" is the position surrounding the first nucleotide that is part of the transcribed sequence, which is also defined as position+1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) are denominated negative.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A constructs of the present disclosure can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule which can play an important role in translation initiation and can also be a genetic component in an expression construct. These additional upstream and downstream regulatory nucleic acid molecules may be derived from a source that is native or heterologous with respect to the other elements present on the promoter construct.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a bacterium, cyanobacterium, animal or a plant into which a heterologous nucleic acid molecule has been introduced. The nucleic acid molecule can be stably integrated into the genome as generally known in the art and disclosed (Sambrook 1989; Innis 1995; Gelfand 1995; Innis & Gelfand 1999). Known methods of PCR include, but are not limited to, methods using paired primers, nested primers, single specific primers, degenerate primers, gene-specific primers, vector-specific primers, partially mismatched primers, and the like. The term "untransformed" refers to normal cells that have not been through the transformation process.

"Wild-type" refers to a virus or organism found in nature without any known mutation.

Design, generation, and testing of the variant nucleotides, and their encoded polypeptides, having the above required percent identities and retaining a required activity of the expressed protein is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide and/or polypeptide variants having, for example, at least 95-99% identity to the reference sequence described herein and screen such for desired phenotypes according to methods routine in the art.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Generally, conservative substitutions can be made at any position so long as the required activity is retained. So-called conservative exchanges can be carried out in which the amino acid which is replaced has a similar property as the original amino acid, for example the exchange of Glu by Asp, Gln by Asn, Val by Ile, Leu by Ile, and Ser by Thr. For example, amino acids with similar properties can be Aliphatic amino acids (e.g., Glycine, Alanine, Valine, Leucine, Isoleucine); Hydroxyl or sulfur/selenium-containing amino acids (e.g., Serine, Cysteine, Selenocysteine, Threonine, Methionine); Cyclic amino acids (e.g., Proline); Aromatic amino acids (e.g., Phenylalanine, Tyrosine, Tryptophan); Basic amino acids (e.g., Histidine, Lysine, Arginine); or Acidic and their Amide (e.g., Aspartate, Glutamate, Asparagine, Glutamine). Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. Amino acid sequence can be modulated with the help of art-known computer simulation programs that can produce a polypeptide with, for example, improved activity or altered regulation. On the basis of this artificially generated polypeptide sequences, a corresponding nucleic acid molecule coding for such a modulated polypeptide can be synthesized in-vitro using the specific codon-usage of the desired host cell. Exemplary conservative substitutions are outlined in the following table.

| Conservative Substitutions I | |
|---|---|
| Side Chain Characteristic | Amino Acid |
| Aliphatic Non-polar | G A P I L V |
| Polar-uncharged | C S T M N Q |
| Polar-charged | D E K R |
| Aromatic | H F W Y |
| Other | N Q D E |

| Conservative Substitutions II | |
|---|---|
| Side Chain Characteristic | Amino Acid |
| Non-polar (hydrophobic) | |
| A. Aliphatic: | A L I V P |
| B. Aromatic: | F W |
| C. Sulfur-containing: | M |
| D. Borderline: | G |

-continued

Uncharged-polar

| | |
|---|---|
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met(M) | Leu, Phe, Ile |
| Phe (F) | Leu, Val, Ile, Ala |
| Pro (P) | Gly |
| Ser (S) | Thr |
| Thr (T) | Ser |
| Trp(W) | Tyr, Phe |
| Tyr (Y) | Trp, Phe, Tur, Ser |
| Val (V) | Ile, Leu, Met, Phe, Ala |

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature (Tm) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $Tm=81.5°\ C.+16.6(\log_{10}[Na^+])+0.41$(fraction G/C content)$-0.63$(% formamide)$-(600/1)$. Furthermore, the Tm of a DNA:DNA hybrid is decreased by 1-1.5° C. for every 1% decrease in nucleotide identity (see e.g., Sambrook and Russel, 2006).

Host cells can be transformed using a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microproj ectile-mediated delivery, receptor-mediated uptake, cell fusion, electroporation, and the like. The transfected cells can be selected and propagated to provide recombinant host cells that comprise the expression vector stably integrated in the host cell genome.

Exemplary nucleic acids which may be introduced to a host cell include, for example, DNA sequences or genes from another species, or even genes or sequences which originate with or are present in the same species, but are incorporated into recipient cells by genetic engineering methods. The term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the cell, DNA from another individual of the same type of organism, DNA from a different organism, or a DNA generated externally, such as a DNA sequence containing an antisense message of a gene, or a DNA sequence encoding a synthetic or modified version of a gene.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Methods of down-regulation or silencing genes are known in the art. For example, expressed protein activity can be down-regulated or eliminated using antisense oligonucleotides, protein aptamers, nucleotide aptamers, and RNA interference (RNAi) (e.g., small interfering RNAs (siRNA), short hairpin RNA (shRNA), and micro RNAs (miRNA) (see e.g., Fanning and Symonds (2006) Handb Exp Pharmacol. 173, 289-303G, describing hammerhead ribozymes and small hairpin RNA; Helene, C., et al. (1992) Ann. N.Y. Acad. Sci. 660, 27-36; Maher (1992) Bioassays 14(12): 807-15, describing targeting deoxyribonucleotide sequences; Lee et al. (2006) Curr Opin Chem Biol. 10, 1-8, describing aptamers; Reynolds et al. (2004) Nature Biotechnology 22(3), 326-330, describing RNAi; Pushparaj and Melendez (2006) Clinical and Experimental Pharmacology and Physiology 33(5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, TX; Sigma Aldrich, MO; Invitrogen). Several siRNA molecule design programs using a variety of algorithms are known to the art (see e.g., Cenix algorithm, Ambion; BLOCK-iT™ RNAi Designer, Invitrogen; siRNA Whitehead Institute Design Tools, Bioinofrmatics & Research Computing). Traits influential in defining optimal siRNA sequences include G/C content at the termini of the siRNAs, Tm of specific internal domains of the siRNA, siRNA length, position of the target sequence within the CDS (coding region), and nucleotide content of the 3' overhangs.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present invention.

Example 1. Synthesis and Characterization of Targeted Nanoclusters and Use Thereof to Perform PET Imaging of NPRC Receptor in a Mouse Angiogenesis Model Patients with carotid atherosclerosis are often asymptomatic and at an unknown risk for stroke. It has been shown that NPR-C receptor is up-regulated in complex and histologically unstable human carotid artery plaque and specific PET imaging of this receptor can be achieved using a CANF peptide functionalized polymeric nanoparticle ($^{64}$Cu-DOTA-CANF-Comb). However, the extended blood retention of this radiotracer results in a relatively long (~12 hr) delay from injection to optimal PET imaging time and potentially increased radiation exposure. This example shows how CANF conjugated gold nanoclusters integrated with $^{64}$Cu ($^{64}$CuAuNCs-CANF) for PET imaging NPR-C expression in a mouse angiogenesis model.

Figure 1B:
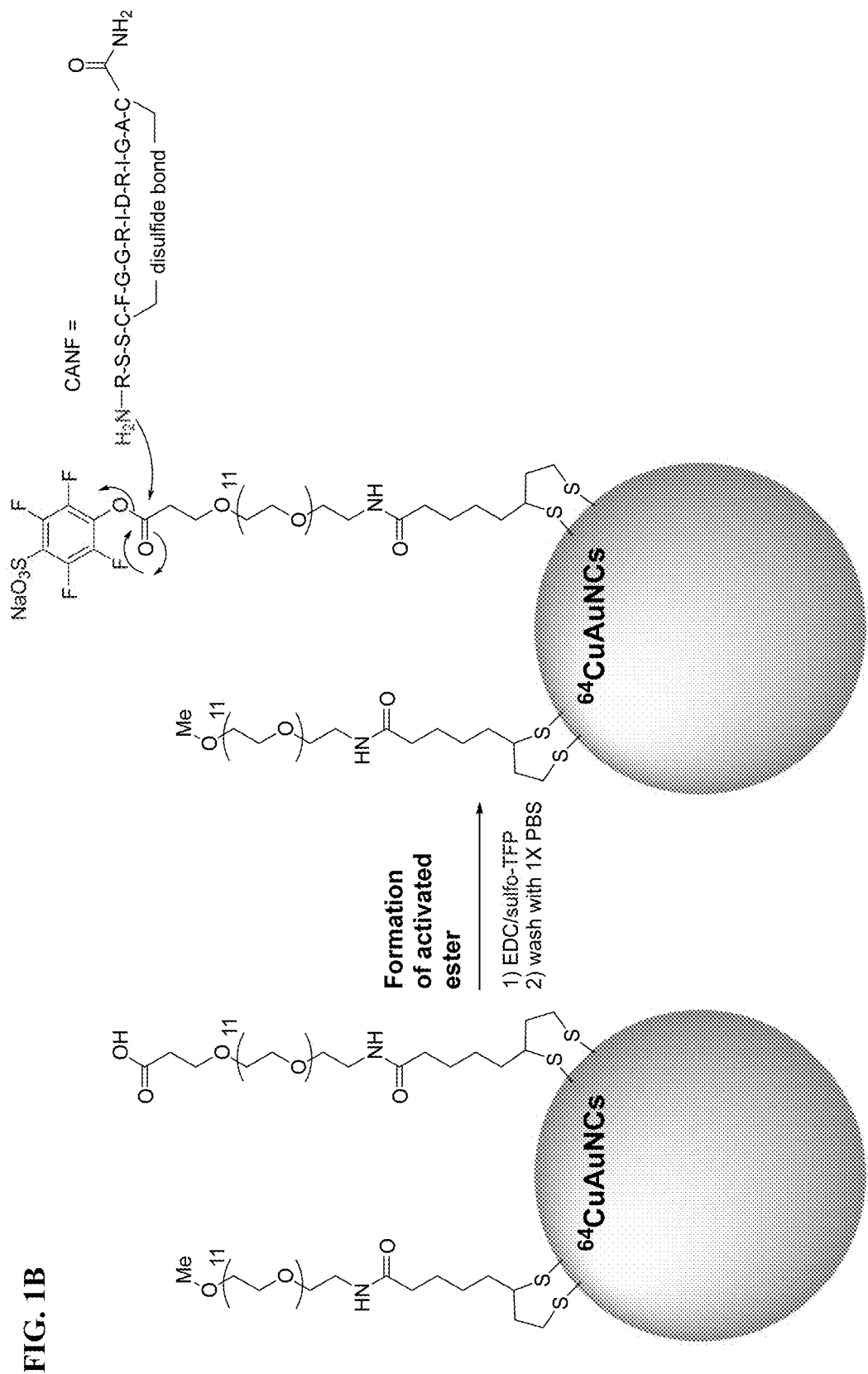
FIG. 1B shows a schematic illustrating the activation of the carboxyl moiety on the $^{64}$Cu—Au nanoclusters.
Figure 1C:
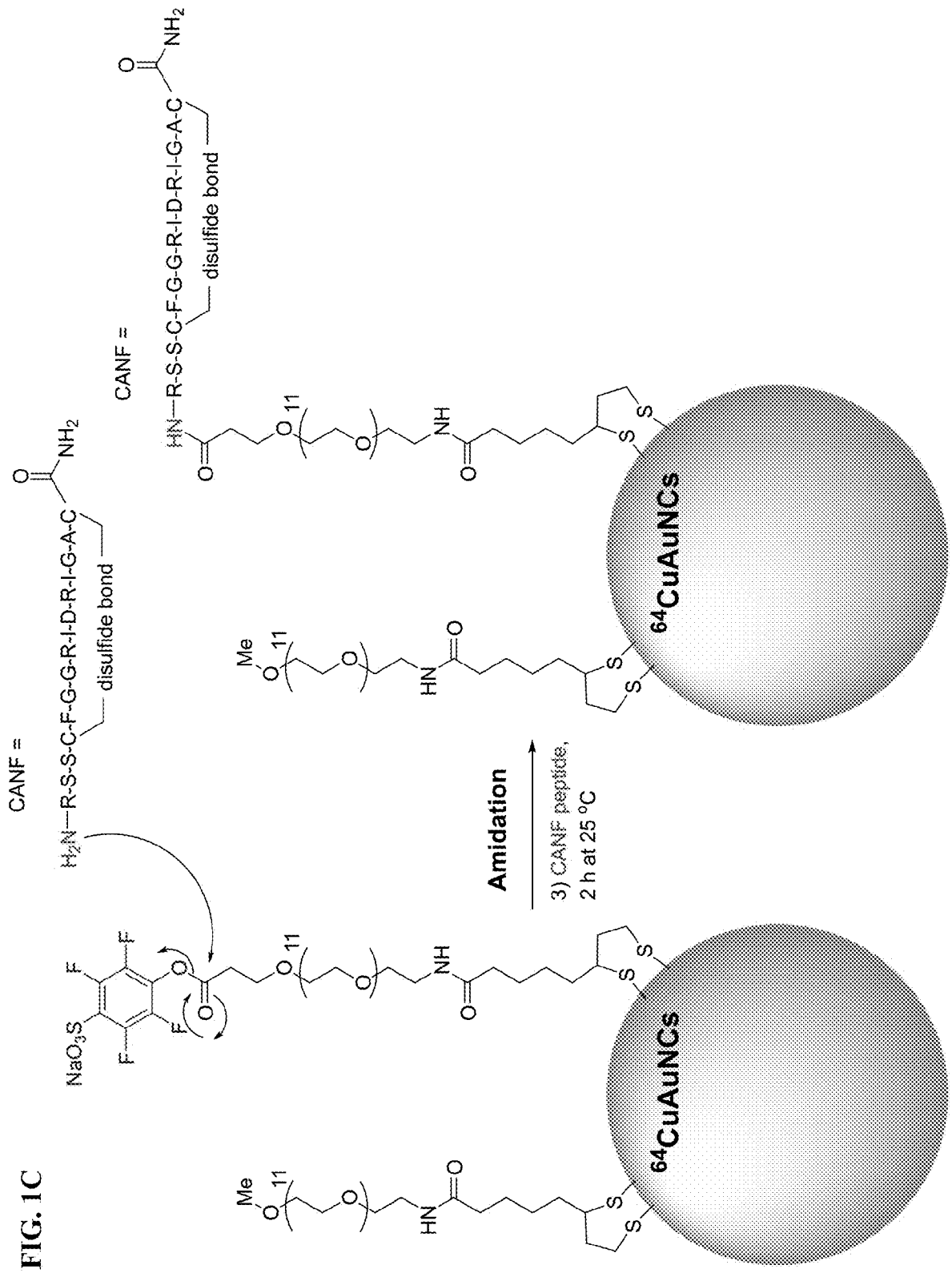
FIG. 1C shows a schematic illustrating the conjugation of a CANF peptide to the $^{64}$Cu—Au nanoclusters via an amidation reaction to the activated carboxyl moieties.

Nanoclusters were synthesized according to the schemes shown in FIGS. 1A-1C. TA-PEG-OMe, TA-PEG-COOH, $^{64}$CuCl$_2$, and HAuCl$_4$ were pre-mixed before the addition of NaBH$_4$ to form a nanocluster functionalized with the TA-PEG-OMe and TA-PEG-COOH moieties (FIG. 1A). The carboxyl end of the TA-PEG-COOH was activated using 1-ethyl-3-(-3-dimethylaminopropyl)carbodiimide hydrochloride (EDC) and 4-sulfo-2,3,5,6-tetrafluorophenol (sulfo-TFP) as shown in FIG. 1B. As shown in FIG. 1C, the CANF peptide was conjugated to the nanoclusters via an amidation reaction to the activated —COOH groups. TA-PEG-OMe, TA-PEG-COOH were purchased from Quanta Biodesign.

Figure 2A:
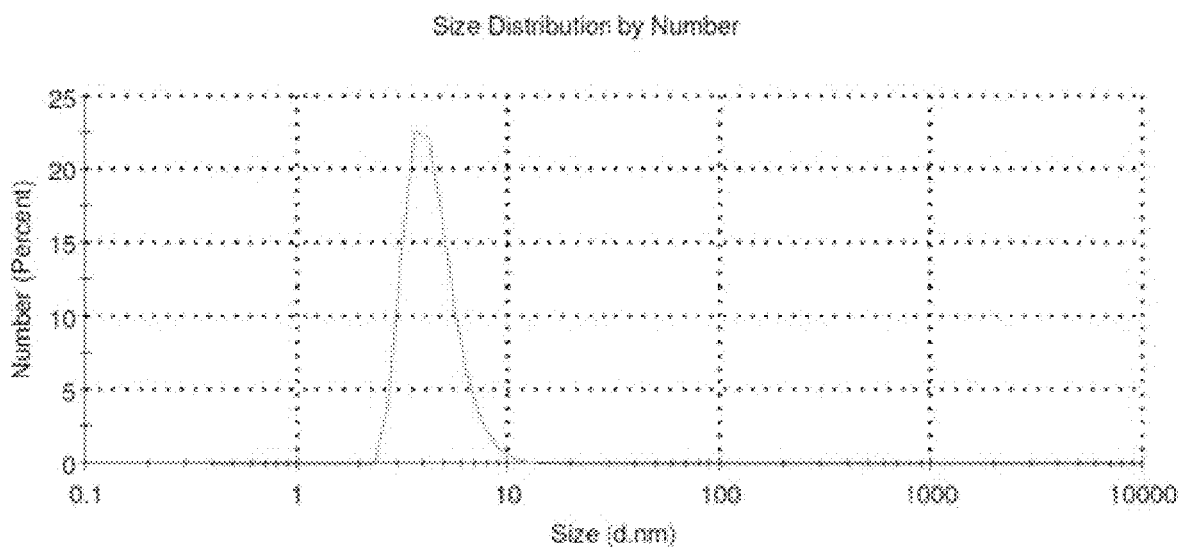
FIG. 2A shows a representative histogram plotting the size distribution of $^{64}$Cu—AuNCs-CANF.
Figure 2B:
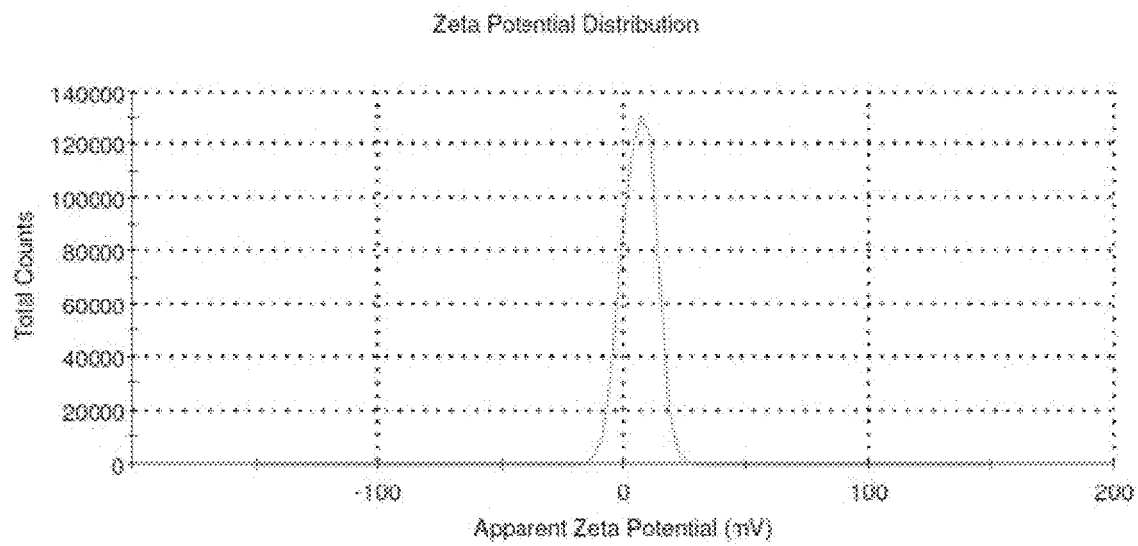
FIG. 2B shows a representative histogram plotting the zinc potential of $^{64}$Cu—AuNCs-CANF.
Figure 2C:
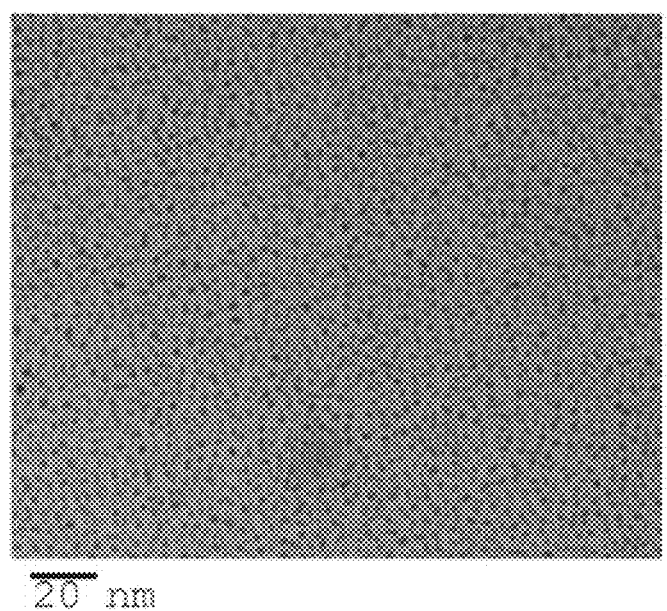
FIG. 2C shows a transmission electron micrograph depicting monodispersed $^{64}$Cu—Au-CANF nanoparticles.

The size and zeta potential of the nanoclusters were characterized with dynamic light scattering and transmission electron microscopy (TEM) and are summarized in Table 1 below and FIGS. 2A-2C. Briefly, the hydrodynamic diameter of $^{64}$CuAuNCs-CANF (4.43±1.34 nm) was slightly larger than that of non-targeted $^{64}$CuAuNCs (3.40±0.77 nm) although TEM demonstrated comparable diameters (2.43±0.49 nm vs. 2.21±0.47 nm). The targeted $^{64}$CuAuNCs-CANF was neutral (5.95±6.29 mV) while the non-targeted $^{64}$CuAuNCs was negatively charged (−40.4±10.1 mV).

TABLE 1

|  | $^{64}$CuAuNCs-COOH | $^{64}$CuAuNCs-CANF |
|---|---|---|
| DLS | 3.40 ± 0.77 nm | 4.43 ± 1.34 nm |
| Zeta Potential | −40.4 ± 10.1 mV | 5.95 ± 6.29 mV |
| TEM | 2.21 ± 0.47 nm | 2.43 ± 0.49 nm |

Figure 4:
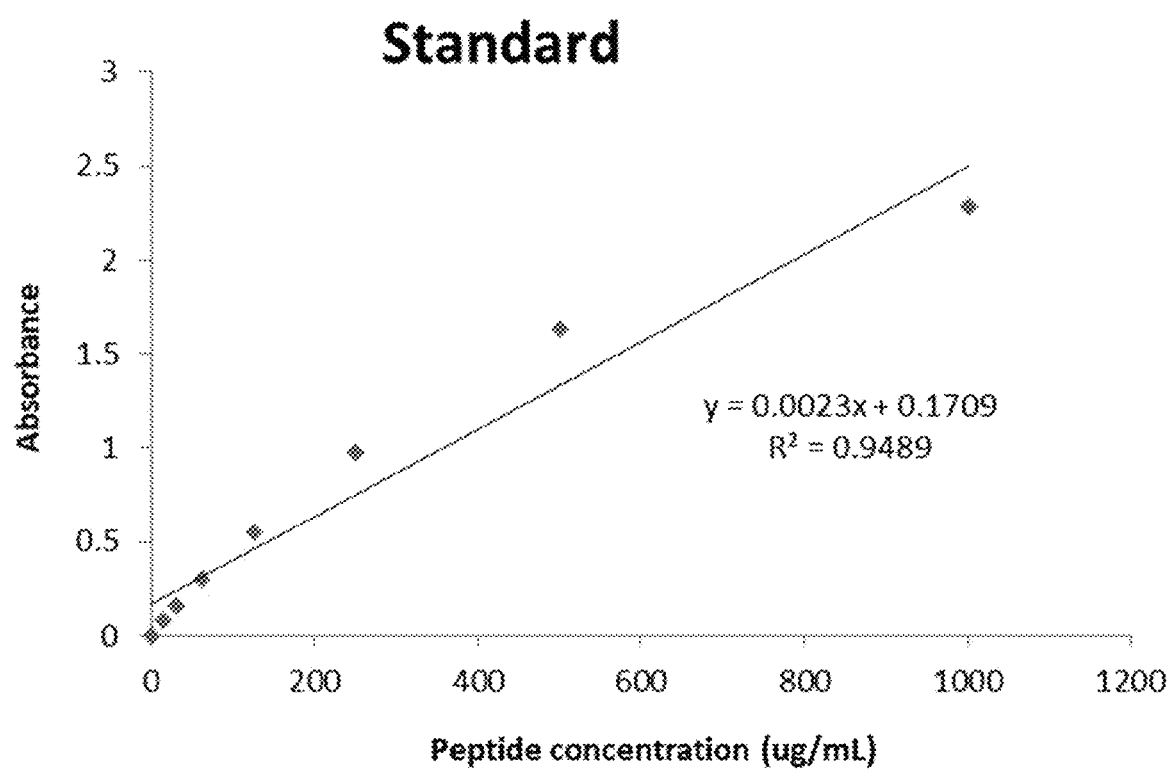
FIG. 4 is a standard curve used to calculate the number of peptides per nanoparticle.

Quantitative colorimetric peptide assay and inductively coupled plasma mass spectrometry were used to determine the number of peptides per nanocluster. ICP-MS determination showed 32.9±4.6 copies of CANF were conjugated on each $^{64}$CuAuNC in an initial batch. In addition, batches were prepared using different ratios of TA-PEGOME to TA-PEG-COOH (either 1:1 or 1:3) to optimize the amount of CANF on each nanocluster. These batches were also analyzed using ICP-MS (standard curve in FIG. 4). Table 2 below lists the number of peptides found conjugated to each nanocluster for the different samples.

TABLE 2

| Sample | Number of Peptides |
|---|---|
| 1:1A | 31-78 CANF |
| 1:1B | 43-100 CANF |
| 1:3A | 89 CANF |
| 1:3B | 21-44 CANF |

Figure 3A:
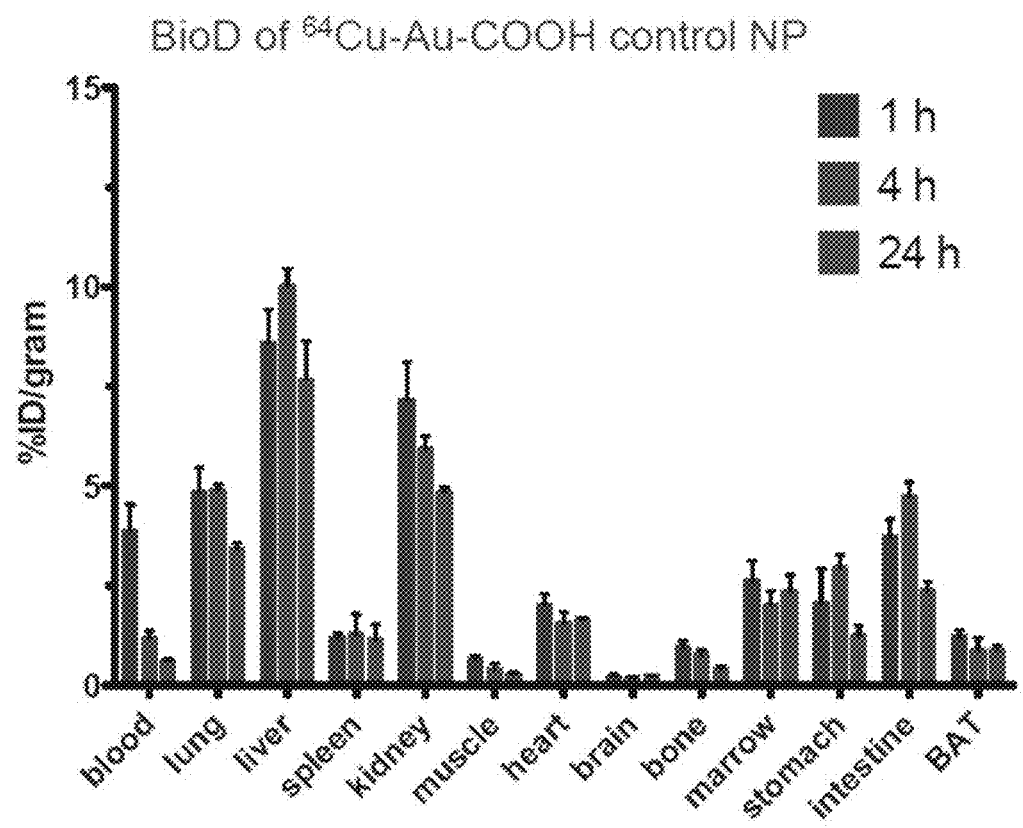
FIG. 3A shows a biodistribution pattern for $^{64}$Cu—Au—COOH—NP in various tissues at 1 h, 4 h and 24 h intervals.
Figure 3B:
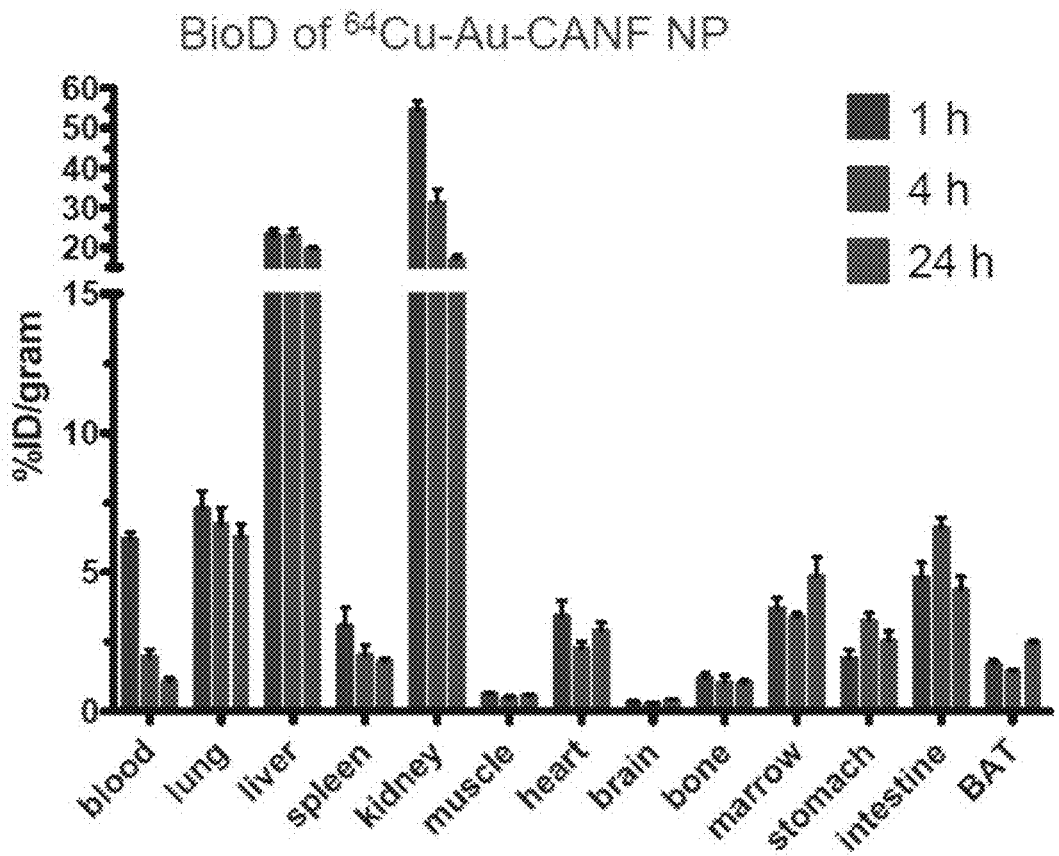
FIG. 3B shows a biodistribution pattern for $^{64}$Cu—Au-CANF-NP in various tissues at 1 h, 4 h and 24 h intervals.
Figure 3C:
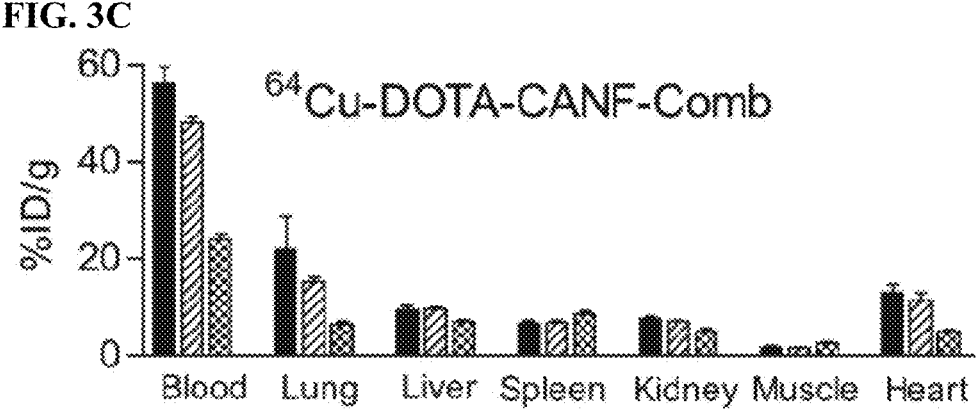
FIG. 3C shows a biodistribution pattern for $^{64}$Cu-DOTA-CANF-Comb in various tissues at 1 h, 4 h and 24 h intervals.

Biodistribution was performed using $^{64}$CuAuNCs-CANF and non-targeted $^{64}$CuAuNCs in wild-type C57Bl/6 mice. Biodistribution of $^{64}$CuAuNCs-CANF showed rapid blood clearance (6.20±0.22, 1.97±0.25, 1.05±0.16% ID/g at 1, 4, and 24 h after injection, respectively, (n=4)), 8-20 times lower than those acquired with the CANF-Comb nanoparticle (56.4±7.54% ID/g, 48.2±2.31% ID/g, and 23.8±2.40% ID/g at each corresponding time points (n=4)). See FIGS. 3A-3C.

Figure 5:
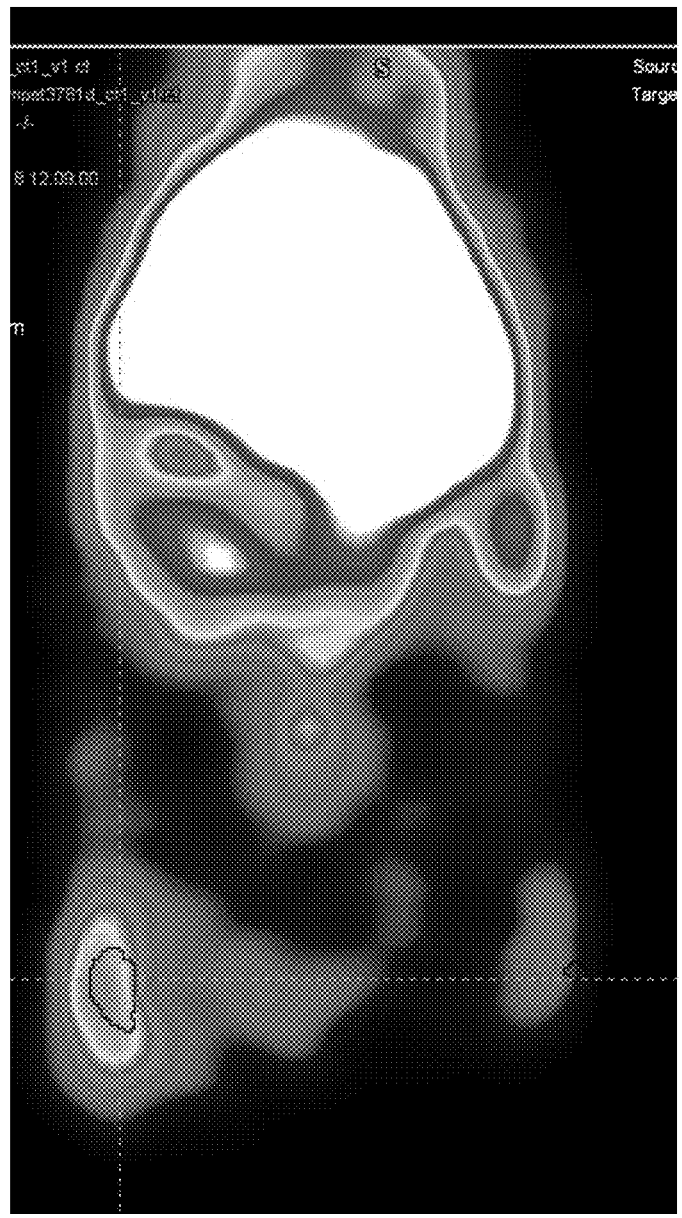
FIG. 5 is an image showing NPRC targeted gold nanoparticles in a Hind Limb Ischemia (HLI) mouse model.

Hind Limb Ischemia (HLI) mouse model was used to assess the targeting of $^{64}$CuAuNCs-CANF using PET. PET imaging with $^{64}$CuAuNCs-CANF (0.700±0.144% ID/g) at 4 h post injection showed significantly (p=0.02, n=4) higher uptake compared to the non-targeted $^{64}$CuAuNCs (0.406±0.133% ID/g) (FIG. 5).

The results in this example, therefore, show the successful synthesis and characterization of the NPRC targeted $^{64}$CuAuNCs-CANF. The rapid blood clearance of $^{64}$CuAuNCs-CANF may allow earlier PET visualization of NPR-C receptor. Initial PET imaging in HLI model indicated the potential of $^{64}$CuAuNCs-CANF for further optimization and assessment of NPR-C targeting in pre-clinical models.

In view of the above, it will be seen that the several objects of the invention are achieved and other advantageous results attained.

As various changes could be made in the above methods, processes, and compositions without departing from the scope of the invention, it is intended that all matter contained in the above description and shown in the accompanying drawings shall be interpreted as illustrative and not in a limiting sense.

The invention claimed is:

1. A composition comprising:
    a nanocluster comprising $^{64}$Cu-Au;
    a natriuretic peptide or fragment thereof having amino acid sequence comprising Arg-Ile-Asp-Arg-Ile (SEQ ID NO: 1); and
    a linking group complexed with the nanocluster and bonded to the natriuretic peptide or fragment thereof.

2. The composition of claim 1 wherein the composition further comprises a surface modifier complexed with the nanocluster.

3. The composition of claim 2 wherein the surface modifier comprises a functionalized polymer.

4. The composition of claim 2 wherein the surface modifier is represented by:

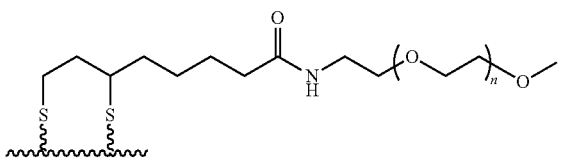

where n is an integer from 5 to 20.

5. The composition of claim 1 wherein the natriuretic peptide or fragment thereof has an amino acid sequence comprising Cys-Phe-Gly-Gly-Arg-Ile-Asp-Arg-Ile-Gly-Ala-Cys-NH$_2$ (SEQ ID NO: 2).

6. The composition of claim 1 wherein the natriuretic peptide or fragment thereof has an amino acid sequence comprising Arg-Ser-Ser-[Cys-Phe-Gly-Gly-Arg-Ile-Asp-Arg-Ile-Gly-Ala-Cys]-NH$_2$ (SEQ ID NO: 3).

7. The composition of claim 1 wherein the natriuretic peptide or fragment thereof comprises C-atrial natriuretic peptide (CANF).

8. The composition of claim 1 wherein the linking group comprises a functionalized polymer.

9. The composition of claim 8 wherein the functionalized polymer comprises ethylene oxide (EO) repeating groups.

10. The composition of claim 9 wherein the functionalized polymer further comprises a thioctic acid moiety.

11. The composition of claim 10 wherein the thioctic acid moiety is complexed with the nanocluster.

12. The composition of claim 8 wherein the linking group is represented by:

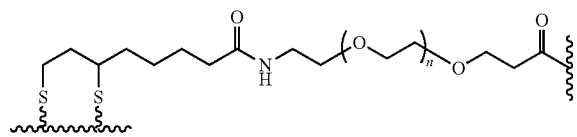

where n is an integer from 5 to 20.

13. A composition comprising:
    a nanocluster comprising $^{64}$Cu-Au;
    a natriuretic peptide or fragment thereof having amino acid sequence comprising Arg-Ile-Asp-Arg-Ile (SEQ ID NO: 1);
    a linking group complexed with the nanocluster and bonded to the natriuretic peptide or fragment thereof, wherein the linking group is represented by:

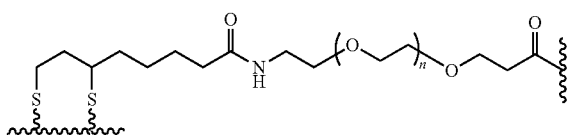

where n is an integer from 5 to 20; and a surface modifier complexed with the nanocluster, wherein the surface modifier is represented by:

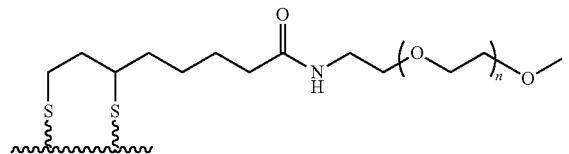

where n is an integer from 5 to 20.

14. The composition of claim 13 wherein the natriuretic peptide or fragment thereof has an amino acid sequence comprising Cys-Phe-Gly-Gly-Arg-Ile-Asp-Arg-Ile-Gly-Ala-Cys-NH$_2$ (SEQ ID NO: 2).

15. The composition of claim 13 wherein the natriuretic peptide or fragment thereof has an amino acid sequence comprising Arg-Ser-Ser-[Cys-Phe-Gly-Gly-Arg-Ile-Asp-Arg-Ile-Gly-Ala-Cys]-NH$_2$ (SEQ ID NO: 3).

16. The composition of claim 13 wherein the natriuretic peptide or fragment thereof comprises C-atrial natriuretic peptide (CANF).

17. A method for determining a distribution of C-type atrial natriuretic peptide receptor or for imaging an atherosclerotic plaque or angiogenesis in a subject, the method comprising administering to the subject the composition of claim 1 and subjecting the subject to a medical imaging procedure.

18. A method for positron emission tomography (PET) imaging of atherosclerotic plaque or cancer in a subject, comprising:
   administering to the subject the composition of claim 1; and
   imaging a distribution of C-type atrial natriuretic peptide receptors in the subject.

19. An imaging agent comprising:
   a nanocluster comprising $^{64}$Cu-Au;
   a linking group; and
   a natriuretic peptide or functional fragment thereof,
wherein the peptide or fragment comprises a sequence Arg-Ile-Asp-Arg-Ile; and
the linking group is operably connected to the nanocluster and the natriuretic peptide.

* * * * *

SEQUENCE LISTING

```
<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: 5 amino acid fragment of natriuretic peptide

<400> SEQUENCE: 1

Arg Ile Asp Arg Ile
1               5

<210> SEQ ID NO 2
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: 12 amino acid fragment of natriuretic peptide
      with carboxy terminal amine
<220> FEATURE:
<221> NAME/KEY: DISULFID
```

```
<222> LOCATION: (1)..(12)
<220> FEATURE:
<221> NAME/KEY: MOD_RES
<222> LOCATION: (12)..(12)
<223> OTHER INFORMATION: AMIDATION

<400> SEQUENCE: 2

Cys Phe Gly Gly Arg Ile Asp Arg Ile Gly Ala Cys
1               5                   10

<210> SEQ ID NO 3
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: 15 amino acid fragment of natriuretic peptide
      with carboxy terminal amine
<220> FEATURE:
<221> NAME/KEY: MISC_FEATURE
<222> LOCATION: (4)..(15)
<223> OTHER INFORMATION: Cys in position 15 is linked to Cys in position
      4 to form a ring.
<220> FEATURE:
<221> NAME/KEY: DISULFID
<222> LOCATION: (4)..(15)
<220> FEATURE:
<221> NAME/KEY: MOD_RES
<222> LOCATION: (15)..(15)
<223> OTHER INFORMATION: AMIDATION

<400> SEQUENCE: 3

Arg Ser Ser Cys Phe Gly Gly Arg Ile Asp Arg Ile Gly Ala Cys
1               5                   10                  15
```